(12) United States Patent
Baliktay et al.

(10) Patent No.: US 9,675,730 B2
(45) Date of Patent: Jun. 13, 2017

(54) JOINT PROSTHESIS MADE FROM A TITANIUM ALLOY

(75) Inventors: Sevki Baliktay, Berlin (DE); Arnold Keller, Kayhude (DE)

(73) Assignee: Waldemar Link GmbH & Co. KG, Hamburg (DE)

(*) Notice: Subject to any disclaimer, the term of this patent is extended or adjusted under 35 U.S.C. 154(b) by 187 days.

(21) Appl. No.: 11/370,163

(22) Filed: Mar. 8, 2006

(65) Prior Publication Data

US 2006/0235536 A1 Oct. 19, 2006

Related U.S. Application Data

(60) Provisional application No. 60/659,097, filed on Mar. 8, 2005.

(51) Int. Cl.
*A61F 2/36* (2006.01)
*A61L 27/06* (2006.01)
(Continued)

(52) U.S. Cl.
CPC .............. *A61L 27/06* (2013.01); *A61F 2/36* (2013.01); *A61F 2/32* (2013.01); *A61F 2/34* (2013.01); *A61F 2/367* (2013.01); *A61F 2/3662* (2013.01); *A61F 2/38* (2013.01); *A61F 2/3804* (2013.01); *A61F 2/40* (2013.01); *A61F 2002/30084* (2013.01); *A61F 2002/30729* (2013.01); *A61F 2002/30827* (2013.01); *A61F 2002/30904* (2013.01); *A61F 2002/30958* (2013.01); *A61F 2002/30986* (2013.01); *A61F 2002/3412* (2013.01); *A61F 2002/3443* (2013.01); *A61F 2002/3611* (2013.01); *A61F 2002/3625* (2013.01); *A61F 2002/3631* (2013.01);
(Continued)

(58) Field of Classification Search
USPC ............................................. 623/18.11, 23.53
See application file for complete search history.

(56) References Cited

U.S. PATENT DOCUMENTS 4,197,643 A 4/1980 Burstone et al.
4,612,066 A 9/1986 Levin et al.
(Continued)

FOREIGN PATENT DOCUMENTS

JP 10-130757 5/1998

OTHER PUBLICATIONS

Ho et al. "Structure and properties of cast binary Ti—Mo alloys". Biomaterials 20 (1990) 2115-2122.*
Zardiackas et al. "Characterization of Ti—15Mo Beta Titanium Alloy". Proceedings of the 1997 16th Southern Biomedical Engineering Conference (1997) 95-98.*
Donachie al. (2000) "Titanium, a Technical Guide," ASM International pp. 39-42.
Phase Diagram of Mo—Ti, Metal Handbook. (1973). vol. 8, ASM, 8th edition; p. 321.
(Continued)

*Primary Examiner* — Christian Sevilla
*Assistant Examiner* — Megan Wolf
(74) *Attorney, Agent, or Firm* — Morrison & Foerster LLP

(57) ABSTRACT

The invention relates to a joint prosthesis having a shaft made from a titanium alloy, in which at least the shaft is investment cast and has a body-centered cubic crystal structure. A titanium alloy having this crystal structure (known as β-titanium alloy) has an advantageously low modulus of elasticity which is well matched to the physiological demands of joint prostheses. Furthermore, implementation as a shaped casting allows a complex shape to be achieved. It is particularly embodied as a femoral prosthesis for an artificial hip joint, which has an elongate shaft with grooves and sawtooth-like projections for bone anchoring.

9 Claims, 3 Drawing Sheets

(51) Int. Cl.
  *A61F 2/32* (2006.01)
  *A61F 2/34* (2006.01)
  *A61F 2/38* (2006.01)
  *A61F 2/40* (2006.01)
  *A61F 2/30* (2006.01)
  *A61F 2/46* (2006.01)

(52) U.S. Cl.
  CPC ............ *A61F 2002/3668* (2013.01); *A61F 2002/4631* (2013.01); *A61F 2310/00023* (2013.01)

(56) References Cited

U.S. PATENT DOCUMENTS

| | | | |
|---|---|---|---|
| 4,857,269 A * | 8/1989 | Wang et al. ................ | 420/417 |
| 4,983,184 A * | 1/1991 | Steinemann ................ | 428/546 |
| 5,226,982 A | 7/1993 | Eylon | |
| 5,947,723 A | 9/1999 | Mottate et al. | |
| 6,200,685 B1 * | 3/2001 | Davidson ................ | 428/472.1 |
| 6,238,491 B1 | 5/2001 | Davidson et al. | |
| 6,409,852 B1 * | 6/2002 | Lin et al. ................ | 148/669 |
| 6,767,418 B1 | 7/2004 | Zhang et al. | |
| 7,288,111 B1 | 10/2007 | Holloway et al. | |
| 2002/0179197 A1 * | 12/2002 | Lin et al. ................ | 148/421 |
| 2004/0088056 A1 * | 5/2004 | Lewallen ................ | 623/22.11 |
| 2004/0136859 A1 * | 7/2004 | Chern Lin et al. ........ | 420/417 |
| 2004/0168751 A1 | 9/2004 | Wu | |
| 2006/0157543 A1 * | 7/2006 | Abkowitz et al. ........ | 228/233.2 |
| 2006/0225818 A1 | 10/2006 | Baliktay | |
| 2007/0068647 A1 | 3/2007 | Baliktay et al. | |

OTHER PUBLICATIONS

Lin et al. (2004). "Comparison Among Mechanical Properties of Investment-cast c.p. Ti, Ti—6Al—7Nb adn Ti—15Mo—1Bi alloys," Material Transactions, The Japan Institute of Metals. 45(10); 3028-3032.
Baliktay et al.; U.S. Office Action, mailed Aug. 21, 2007, directed to U.S. Appl. No. 11/370,231; (8 pages).
Baliktay et al.; U.S. Office Action, mailed Mar. 17, 2008, directed to U.S. Appl. No. 11/370,231; (9 pages).
Baliktay et al.; U.S. Office Action, mailed Oct. 7, 2008, directed to U.S. Appl. No. 11/370,231; (8 pages).
Baliktay et al.; U.S. Office Action, mailed Mar. 30, 2009, directed to U.S. Appl. No. 11/370,231; (8 pages).
Baliktay; U.S. Office Action, mailed Aug. 21, 2007, directed to U.S. Appl. No. 11/370,232; (6 pages).
Baliktay; U.S. Office Action, mailed Mar. 6, 2008, directed to U.S. Appl. No. 11/370,232; (8 pages).
Baliktay; U.S. Office Action, mailed Oct. 7, 2008, directed to U.S. Appl. No. 11/370,232; (8 pages).
Baliktay; U.S. Office Action, mailed Mar. 30, 2009, directed to U.S. Appl. No. 11/370,232; (8 pages).
"Annealing (Metallurgy)", Wikipedia, Aug. 2009.
Baliktay, S., U.S. Office Action mailed on Sep. 8, 2009, directed to a related U.S. Appl. No. 11/370,231; 9 pages.
Baliktay, S. et al., U.S. Office Action mailed on Sep. 8, 2009, directed to a related U.S. Appl. No. 11/370,232; 11 pages.
Baliktay; U.S. Office Action, mailed Dec. 15, 2009, directed to U.S. Appl. No. 11/370,232; (9 pages).
Baliktay et al.; U.S. Office Action, mailed Dec. 16, 2009, directed to U.S. Appl. No. 11/370,231; (9 pages).

* cited by examiner

| Solution annealing temperature [°C] | Tensile strength Rm [N/mm²] | 0.2% Proof stress Rp [N/mm²] | Elongation at break A5 [%] | Reduction of area after fracture Z [%] | Modulus of elasticity E [kN/mm²] | Hardness HB30 |
|---|---|---|---|---|---|---|
| 700 | 920 | 916 | 2.1 | 10 | 68 | 285 |
| 740 | 841 | 665 | 7.5 | 19.3 | 66 | 278 |
| 760 | 790 | 545 | 18.5 | 23.4 | 65.4 | 268 |
| 780 | 735.3 | 520 | 27.4 | 40 | 63.7 | 260 |
| 800 | 725 | 505 | 37.6 | 52 | 59.4 | 255 |

Fig. 5

JOINT PROSTHESIS MADE FROM A TITANIUM ALLOY

REFERENCE TO RELATED APPLICATION

This application claims priority from U.S. Provisional Application Ser. No. 60/659,097, filed Mar. 8, 2005, the entire content of which is incorporated herein by reference.

FIELD OF THE INVENTION

The invention relates to a joint prosthesis having a shaft made from a titanium alloy.

BACKGROUND OF THE INVENTION

The major joints of the human body are subject to high mechanical stresses. For example, the joints of the locomotor apparatus have to bear a large part of the body's weight, and moreover they are moved every time a step is taken. Therefore, the bones which support the joints have a powerful cortical structure. Their integrity is important for sufficient functioning of the joint. The same is true of the arm joints; although the weight which they have to support is lower, they are moved more frequently and are therefore exposed to high levels of wear. Moreover, their dimensions are smaller and they are more susceptible to injury.

Prostheses intended for permanent implantation (endoprostheses) not only have to have sufficient mechanical properties to ensure the desired functionality, but also have to have a biocompatibility that is as high as possible to ensure that they are tolerated by the patient over a prolonged period of time. In particular the latter aspect is very important, since any incompatibilities which occur generally require explantation of the prosthesis. This equates to failure of the prosthesis.

It is known that inadequate transmission of load from the prosthesis to the surrounding bone can lead to degeneration of the bone tissue. This often leads to the prosthesis coming loose. Therefore, to avoid this degeneration, it is important to ensure loading that is as physiological as possible by the prosthesis. Tests have shown that hip prostheses with a lower modulus of elasticity produce a loading situation which is more physiological than when using rigid prostheses. For example, in the case of femoral prostheses, there has been a move away from cobalt-chromium alloys, which generally have a very high modulus of elasticity in the region of approx. 200 000 N/mm$^2$, toward titanium alloys, which have a lower modulus of elasticity, such as for example TiAl6V4, the modulus of which is approx. 100 000 N/mm$^2$. However, these levels are still well above the modulus of elasticity of the cortical bone, at approx. 25 000 N/mm$^2$.

SUMMARY OF THE INVENTION

The invention is based on the object of improving a joint prosthesis of the type described in the introduction in such a way as to achieve more physiological transmission of load.

The solution according to the invention lies in the features of the invention as broadly described herein. Advantageous refinements form the subject matter of the preferred embodiments.

According to the invention, in a joint prosthesis having a shaft made from a titanium alloy, it is provided that at least the shaft is investment-cast and has a body-centered cubic crystal structure (known as β-titanium alloy).

It has been found that the joint prosthesis according to the invention can be used to achieve a significantly lower modulus of elasticity. Depending on the titanium alloy used and the heat treatment carried out, it is possible to reach moduli of elasticity of approx. 60 000 N/mm$^2$. This corresponds to virtually half the modulus of elasticity which has previously been achieved with titanium alloys. Furthermore, the invention provides for at least the shaft to be investment-cast. This allows more complex shaping of the prosthesis. The forging processes which have hitherto primarily been used for titanium prostheses only allow the production of relatively simple structures. This restriction is overcome by the invention. Consequently, the prostheses according to the invention can be better matched to the loads which are to be absorbed. For example, the shaping of the prosthesis may vary more finely according to the local stresses. The prosthesis only has to be of stronger and therefore more rigid dimensions in specifically the regions in which high stresses occur; in the other regions, it can be of weaker and therefore more elastic design. This allows the matching of the prosthesis to the anatomical conditions to be further improved. Moreover, it is easy for securing elements, such as projections, to be formed integrally with the prosthesis. It is possible to provide a greater number of and more complex securing elements. Therefore, the prosthesis is more suitable for cement-free implantation. The benefit of the invention is that complex shapes which cannot be practically realized by forging processes can be achieved even for prostheses made from β-titanium alloys. In general, it will be the case that the prosthesis together with the shaft is investment-cast and heat-treated in one, near net shape piece, although the possibility of assembling the prosthesis from a plurality of parts including the shaft should not be ruled out.

The invention can advantageously be used for artificial hip joints, in particular for femoral prostheses. These are among the most highly stressed prostheses and have a shaft of complicated shape for implantation in the femur. It has been found that degeneration phenomena readily occur in particular in the upper region of the femur if a prosthesis that is too rigid has been implanted. This often leads to failure of the prosthesis. In the case of a femoral prosthesis according to the invention, the modulus of elasticity is considerably lower and therefore much closer to a physiological level of the bone material in the upper region of the femur. The femoral prosthesis according to the invention successfully counteracts the risk of degeneration. The same applies to an embodiment in the form of a knee prosthesis, which generally have very long shafts.

It is preferable for the titanium alloy to be a titanium-molybdenum alloy. The addition of molybdenum stabilizes what is known as the β-phase of the titanium alloy. This allows the formation of the desired body-centered cubic crystal structure. Molybdenum as alloying element has a lower toxicity than other alloying elements which likewise stabilize the β-phase, in particular niobium or vanadium. The reduction in the toxicity is an important benefit of a prosthesis intended for long-term implantation.

The level of the molybdenum or molybdenum equivalent in the alloy is expediently in the range from 7.5 to 25%. The result of this, in particular in the case of a molybdenum content of at least 10%, is sufficient stabilization of the β-phase all the way down to the room temperature range. The content is preferably between 12 and 16%. This allows a meta-stable β-phase to be achieved by rapid cooling after casting. The mean grain size of the crystal structure is at least 0.3 mm, preferably 0.5 mm. There is generally no need to add further alloy-forming elements. In particular, there is no need to add vanadium or aluminum. The elimination of these elements has the advantage, which has already been mentioned above, that it is possible to avoid the toxicity emanating from these alloy-forming elements. The same applies to bismuth, the biocompatibility of which likewise does not match that of titanium. Furthermore, the titanium-molybdenum alloy has the advantage of having improved mold filling properties compared to known alloys such as TiAl6V4. This makes it possible to form sharper-edged structures by the investment casting process.

It has proven particularly suitable for at least the shaft of the prosthesis according to the invention to be hot isostatically pressed and solution annealed. It has been found that considerable improvements with regard to brittleness are achieved with a material which has been heat-treated in this way. The hot isostatic pressing, in addition to the usual advantages of eliminating microporosity, also dissolves inter-dendritic precipitations. A temperature below the β-transus temperature, specifically at most 100° C., preferably 40° C., below the β-transus temperature, is expedient. Temperatures in the range from 710° C. to 760° C., preferably of approx. 740° C., have proven suitable for a titanium-molybdenum alloy with a molybdenum content of 15%. The solution annealing improves the ductility of the alloy. Temperatures of at least 700° C. up to 900° C., preferably in the range from 780° C. to 880° C., have proven suitable for this purpose. There is no need for a preliminary age-hardening before or after the hot-isostatic pressing. For cooling after the solution annealing, the shaft is expediently quenched in water.

BRIEF DESCRIPTION OF THE DRAWINGS

The invention is explained in more detail below with reference to the drawing, which illustrates an advantageous exemplary embodiment and in which:

FIG. 4 shows an image of the crystal structure after hot isostatic pressing and solution annealing; and FIG. 5 shows a table giving mechanical properties of the prosthesis according to the invention.

DETAILED DESCRIPTION OF THE INVENTION

Figure 1:
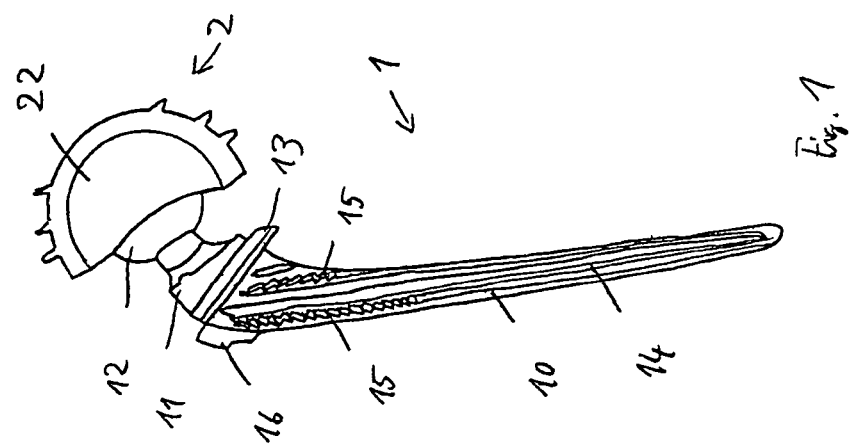
FIG. 1 shows a diagrammatic view of a first exemplary embodiment of a joint prosthesis according to the invention.

The exemplary embodiment illustrated in FIG. 1 shows a femoral prosthesis for an artificial hip joint. The femoral prosthesis 1 consists of a n-titanium alloy, namely TiMo15. This alloy has a body-centered cubic crystal structure at room temperature.

The femoral prosthesis 1 is intended for implantation at the upper end of the femur. It can interact with an acetabulum component 2 which has been implanted in the pelvic bone. The femoral prosthesis 1 has an elongate shaft 10 as bone anchoring element and a neck 11 which adjoins it at an obtuse angle. At its end remote from the shaft there is arranged a joint head 12 which, together with a bearing insert 22 of the acetabulum component 2, forms a ball joint. Implantation involves complete or partial resection of the head of the thighbone neck, opening up access to the medullary cavity of the femur. This access is used to introduce the shaft 10 of the femoral prosthesis 1 into the medullary cavity, where it is anchored. Depending on the particular embodiment, cement is provided as anchoring means or the fixing is effected without the use of cement.

The femoral prosthesis 1 introduces mechanical loads acting on the hip joint, whether static loads when standing or dynamic loads when walking, into the femur. Physiologically compatible transmission of loads is important for permanent reliable anchoring of the femoral prosthesis 1 in the bone material of the femur. If the femoral prosthesis 1 is of very rigid design, it absorbs a considerable portion of the load, thereby relieving the load on the bone material in particular in the upper region of the femur. In the longer term, this leads to degeneration of the femur in this region. This leads to the risk of the femoral prosthesis 1 coming loose and ultimately of the prosthesis failing. To prevent this failure mode, it is known per se for the femoral prosthesis 1 to be of less rigid, i.e. more elastic with a physiologically favorable low modulus of elasticity design. In particular the shaft 10 of the femoral prosthesis 1 is critical in this respect. In the cortical region, the bone material of the femur has a modulus of elasticity of approx. 20 000 to 25 000 $N/mm^2$. According to the invention, the femoral prosthesis 1 has a modulus of elasticity of approx. 60 000 $N/mm^2$. This is a favorable modulus which is much lower than that of materials which are conventionally used, such as TiAl6V4. These materials have a modulus of elasticity of approx. 100 000 $N/mm^2$ or even 200 000 $N/mm^2$ in the case of cobalt-chromium alloys.

The invention allows simple production of even complex shapes by investment casting. For example, the femoral prosthesis 1 has a multiplicity of recesses and sawtooth-like projections on its shaft 10. These are used to improve anchoring of the femoral prosthesis 1 in the femur, allowing cement-free implantation. A plurality of grooves 14 are provided running in the longitudinal direction of the shaft 10. They are arranged on both the anterior and posterior side of the shaft 10 but may also be provided on the lateral sides. A plurality of rows of sawtooth projections 15 are provided in the upper region of the shaft 10. Furthermore, an encircling ring 13 is provided at the transition to the neck 11. It can be designed as a separate element, but the invention means that it may also be integral with the shaft 10 and neck 11. In general, a single-piece design of the prosthesis is preferred, with the exception of exchangeable or optional attachment parts or wearing parts. Furthermore, a fixing projection 16 is provided on the shaft 10 adjacent to the ring 13 to prevent rotation. Such complex shapes of joint prostheses can conventionally only be produced from TiAl6V4. However, this material has a different, less favorable crystal structure and therefore an undesirably high modulus of elasticity.

Figure 2:
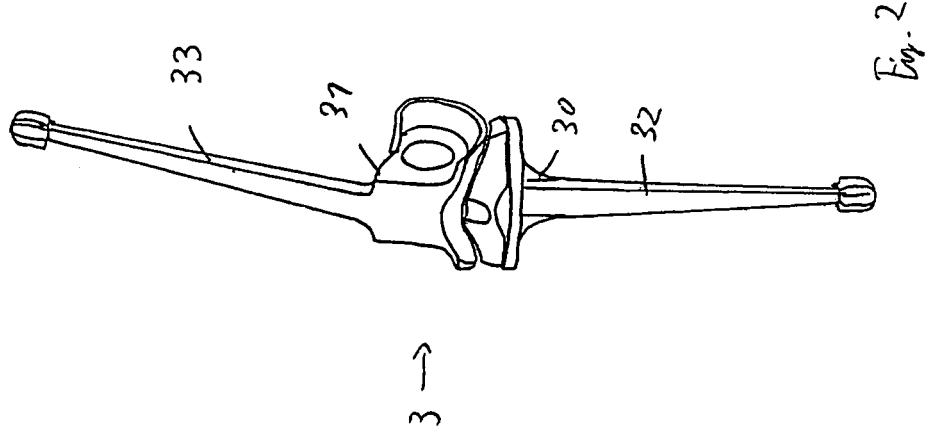
FIG. 2 shows a diagrammatic view of a further exemplary embodiment of a joint prosthesis according to the invention.

The invention can advantageously also be used for other types of joint prostheses. FIG. 2 illustrates a knee prosthesis 3 as a further exemplary embodiment. It comprises a femur component 31 and a tibia component 30. The femur component 31 has a long shaft 33 as bone anchoring element. It is designed for implantation in the medullary cavity of the femur, which has been opened up by section of the natural knee joint. As in the case of the femoral prosthesis, in this case too the problem of degeneration of the surrounding cortical structure occurs if the knee prosthesis 3, in particular its shaft 33, is made too rigid. The same applies to a shaft 32 of the tibia component 30.

The joint prosthesis according to the invention can also be used for other joints, for example at the elbow or the shoulder.

The text which follows describes a way of carrying out the invention.

The starting material is a β-titanium alloy with a molybdenum content of 15% (TiMo15). This alloy is commercially available in the form of billets (ingots).

Figure 3:
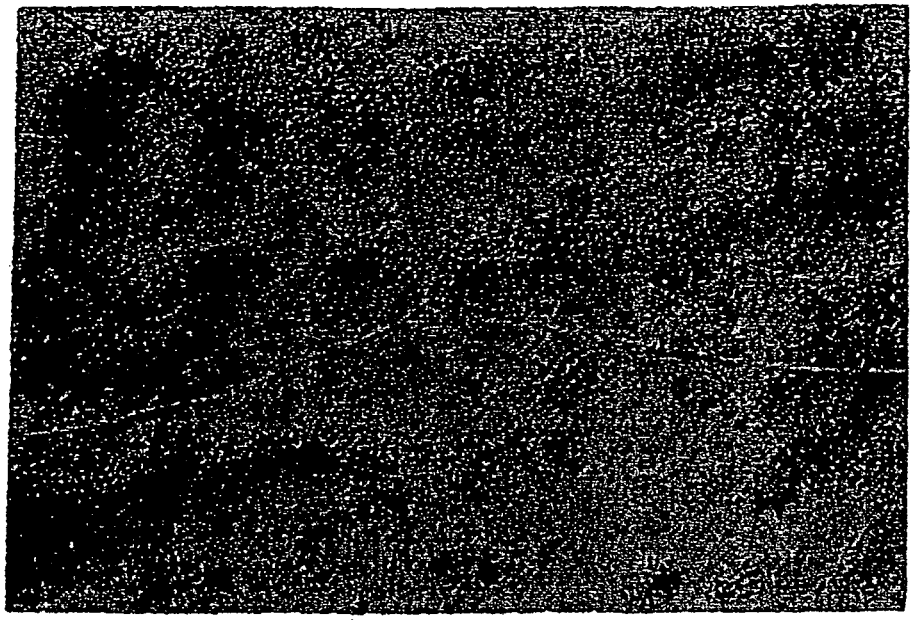
FIG. 3 shows an image of the crystal structure immediately after the investment casting (magnified 1000 times)
Figure 6:
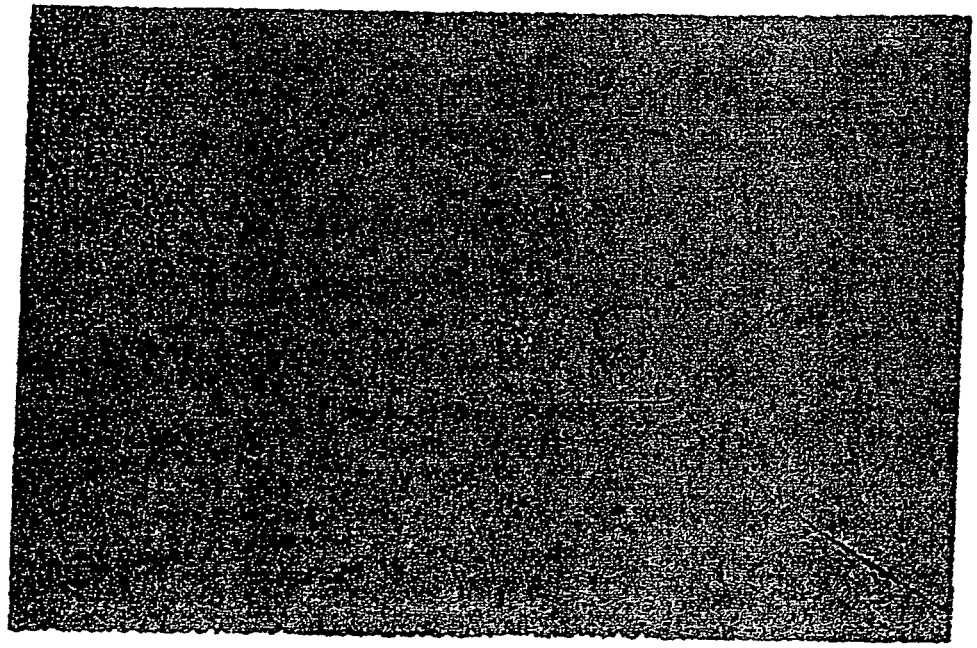

A first step involves investment casting of the parts of the hip prosthesis. A casting installation is provided for the purpose of melting and casting the TiMo15. The casting installation is preferably a cold-wall crucible vacuum induction melting and casting installation. An installation of this type can reach the high temperatures which are required for reliable melting of TiMo15 for investment casting. The melting point of TiMo15 is 1770° C. plus a supplement of approx. 60° C. for reliable investment casting. Overall, therefore, a temperature of 1830° C. needs to be reached. The investment casting of the melt is then carried out by means of processes which are known per se, for example using ceramic molds as lost mold. Investment casting techniques of this type are known for the investment casting of TiAl6V4. The result is a body-centered cubic crystal structure. An image of the microstructure is illustrated in FIG. 3.

The castings, from which the casting molds have been removed after the investment casting, are subjected to a heat treatment. This involves hot isostatic pressing (HIP) at a temperature just below the β-transus temperature. This temperature may be in the range from 710° C. to 760° C. and is preferably approximately 740° C. at an argon pressure of 1100 to 1200 bar. During this treatment, inter alia undesirable precipitations in inter-dendritic zones are dissolved. It is expedient first of all for a surface zone which may have formed during casting in the form of a hard, brittle layer (known as the α-case) to be removed by pickling. This layer is usually approx. 0.03 mm thick.

Following the hot-isostatic pressing, the castings have only a low ductility. It is assumed that this embrittlement is attributable to secondary precipitations during the hot isostatic pressing and the subsequent, generally slow cooling from the hot isostatic pressing temperature.

To dissolve these disruptive precipitations, the castings are annealed in a chamber furnace under argon shielding gas atmosphere. A temperature range from approx. 780° C. to 860° C. for a duration of several hours, generally two hours, is selected for this purpose. In this context, there is a reciprocal relationship between the temperature and the duration; a shorter time is sufficient at higher temperatures, and vice versa. After the solution annealing, the castings are quenched using cold water. The resulting microstructure is illustrated in FIG. 4.

The mechanical properties achieved after solution annealing are reproduced in the table shown in FIG. 5.

It can be seen that the modulus of elasticity drops as the temperature rises during the solution annealing, specifically from 68 000 N/mm² down to levels of as low as 59 400 N/mm². The ductility values improve with decreasing strength and hardness. For example, after solution annealing for two hours at 800° C., the result is a modulus of elasticity of approx. 60 000 N/mm² with an elongation at break of approx. 40% and a fracture strength Rm of approx. 730 N/mm².

The invention claimed is:

1. A joint prosthesis, comprising:
   a shaft consisting essentially of a β-titanium alloy, at least the shaft being produced by an investment casting process and the β-titanium alloy of the shaft having a body centered cubic crystal structure and having a modulus of elasticity between 59.4 kN/mm² and 68 kN/mm²,
   wherein the shaft is shaped for implantation into a medullary cavity of a human femur,
   wherein the β-titanium alloy consists of titanium and molybdenum, and
   wherein the β-titanium alloy has a molybdenum content in the range between 12% and 16% by weight of the alloy.

2. The joint prosthesis of claim 1, wherein the joint prosthesis is configured in a shape of a femoral prosthesis.

3. The joint prosthesis of claim 1, wherein the joint prosthesis is configured in a shape of a knee prosthesis.

4. The joint prosthesis of claim 1, wherein the shaft is subjected during production to hot isostatic pressing and solution annealing.

5. The joint prosthesis of claim 4, wherein the hot isostatic pressing is performed at a temperature which is at most equal to a beta transus temperature of the β-titanium alloy and is not less than a temperature that is 100° C. below the beta transus temperature.

6. The joint prosthesis of claim 4, wherein the hot isostatic pressing is performed at a temperature that is at most a beta transus temperature of the β-titanium alloy and is not less than a temperature that is 40° C. below the beta transus temperature.

7. The joint prosthesis of claim 1, wherein the body centered cubic crystal structure has a mean grain size of at least 0.5 mm.

8. The joint prosthesis of claim 1, wherein the body centered cubic crystal structure has a mean grain size of at least 0.3 mm.

9. The joint prosthesis of claim 1, wherein the molybdenum content is 15% by weight of the alloy.

* * * * *